United States Patent
Shelton, IV et al.

(10) Patent No.: US 9,848,877 B2
(45) Date of Patent: Dec. 26, 2017

(54) METHODS AND DEVICES FOR ADJUSTING A TISSUE GAP OF AN END EFFECTOR OF A SURGICAL DEVICE

(71) Applicant: Ethicon Endo-Surgery, Inc., Cincinnati, OH (US)

(72) Inventors: Frederick E. Shelton, IV, Hillsboro, OH (US); Emily A. Schellin, Cincinnati, OH (US); Michael J. Vendely, Lebanon, OH (US); Jason L. Harris, Lebanon, OH (US); Adam R. Dunki-Jacobs, Cincinnati, OH (US)

(73) Assignee: Ethicon LLC, Guaynabo, PR (US)

(*) Notice: Subject to any disclaimer, the term of this patent is extended or adjusted under 35 U.S.C. 154(b) by 487 days.

(21) Appl. No.: 14/474,952

(22) Filed: Sep. 2, 2014

(65) Prior Publication Data

US 2016/0058450 A1 Mar. 3, 2016

(51) Int. Cl.
*A61B 17/10* (2006.01)
*A61B 17/04* (2006.01)
*A61B 17/072* (2006.01)

(52) U.S. Cl.
CPC ..... *A61B 17/07207* (2013.01); *A61B 2017/0725* (2013.01); *A61B 2017/07228* (2013.01); *A61B 2017/07271* (2013.01); *A61B 2017/07278* (2013.01); *A61B 2017/07285* (2013.01)

(58) Field of Classification Search
CPC ........ A61B 2017/07271; A61B 17/068; A61B 17/105; A61B 2017/07278
USPC .......................................... 227/175.1–182.1
See application file for complete search history.

(56) References Cited

U.S. PATENT DOCUMENTS

| | | | |
|---|---|---|---|
| 4,712,545 A | * 12/1987 | Honkanen | A61B 17/1608 600/564 |
| 5,413,268 A | * 5/1995 | Green | A61B 17/07207 227/176.1 |
| 5,465,895 A | 11/1995 | Knodel et al. | |
| 5,725,536 A | 3/1998 | Oberlin et al. | |
| 7,000,818 B2 | 2/2006 | Shelton, IV et al. | |
| 7,473,258 B2 | 1/2009 | Clauson et al. | |
| 7,533,790 B1 | 5/2009 | Knodel et al. | |
| 7,641,671 B2 | 1/2010 | Crainich | |

(Continued)

FOREIGN PATENT DOCUMENTS

| | | |
|---|---|---|
| EP | 1943963 A2 | 7/2008 |
| EP | 2732772 A1 | 5/2014 |

(Continued)

OTHER PUBLICATIONS

"MicroCutter XCHANGE™ 30." Inservice Poster. (Oct. 13).

(Continued)

*Primary Examiner* — Robert Long
(74) *Attorney, Agent, or Firm* — Mintz Levin Cohn Ferris Glovsky and Popeo, P.C.

(57) ABSTRACT

Devices and methods are provided for adjusting a tissue gap of an end effector of a surgical device. In general, a surgical device can be configured to have an adjustable gap of space between a cartridge jaw and an anvil of the device's end effector when the end effector is in a closed position. The end effector can be configured to removably seat a cartridge therein. The cartridge can be configured to define the gap of space between the cartridge jaw and the anvil when the end effector is in the closed position.

7 Claims, 12 Drawing Sheets

(56) References Cited

U.S. PATENT DOCUMENTS

| | | | |
|---|---|---|---|
| 7,669,746 B2 | 3/2010 | Shelton, IV | |
| 7,678,121 B1 | 3/2010 | Knodel | |
| 7,753,250 B2 | 7/2010 | Clauson et al. | |
| 7,918,376 B1 | 4/2011 | Knodel et al. | |
| 7,954,683 B1 | 6/2011 | Knodel et al. | |
| 7,963,432 B2 | 6/2011 | Knodel et al. | |
| 7,988,026 B2 | 8/2011 | Knodel et al. | |
| 8,056,789 B1 | 11/2011 | White et al. | |
| 8,066,720 B2 | 11/2011 | Knodel et al. | |
| 8,070,034 B1 | 12/2011 | Knodel | |
| 8,070,036 B1 | 12/2011 | Knodel | |
| 8,087,562 B1 | 1/2012 | Manoux et al. | |
| 8,123,795 B1 | 2/2012 | Knodel et al. | |
| 8,261,958 B1 | 9/2012 | Knodel | |
| 8,272,551 B2 | 9/2012 | Knodel et al. | |
| 8,317,071 B1 | 11/2012 | Knodel | |
| 8,317,072 B1 | 11/2012 | Knodel et al. | |
| 8,356,740 B1 | 1/2013 | Knodel | |
| 8,357,174 B2 | 1/2013 | Roth et al. | |
| 8,365,973 B1 | 2/2013 | White et al. | |
| 8,403,956 B1 | 3/2013 | Thompson et al. | |
| 8,439,245 B2 | 5/2013 | Knodel et al. | |
| 8,439,246 B1 | 5/2013 | Knodel | |
| 8,496,155 B2 | 7/2013 | Knodel | |
| 8,505,800 B1 | 8/2013 | Knodel et al. | |
| 8,556,153 B1 | 10/2013 | Knodel | |
| 8,631,992 B1 | 1/2014 | Hausen et al. | |
| 8,636,189 B1 | 1/2014 | Knodel et al. | |
| 8,679,155 B2 | 3/2014 | Knodel et al. | |
| 8,701,960 B1 | 4/2014 | Manoux et al. | |
| 2005/0006431 A1* | 1/2005 | Shelton | A61B 17/07207 227/175.1 |
| 2005/0178813 A1* | 8/2005 | Swayze | A61B 17/07207 227/176.1 |
| 2006/0053563 A1* | 3/2006 | Skinner | B25B 7/10 7/127 |
| 2008/0296347 A1* | 12/2008 | Shelton, IV | A61B 17/072 227/180.1 |
| 2009/0065552 A1 | 3/2009 | Knodel et al. | |
| 2010/0155453 A1 | 6/2010 | Bombard et al. | |
| 2010/0213240 A1* | 8/2010 | Kostrzewski | A61B 17/072 227/180.1 |
| 2011/0036892 A1* | 2/2011 | Marczyk | A61B 17/07207 227/176.1 |
| 2011/0155781 A1* | 6/2011 | Swensgard | A61B 17/07207 227/176.1 |
| 2011/0204120 A1 | 8/2011 | Crainich | |
| 2011/0278343 A1* | 11/2011 | Knodel | A61B 17/07207 227/176.1 |
| 2012/0010652 A1 | 1/2012 | Hahnen et al. | |
| 2012/0223121 A1* | 9/2012 | Viola | A61B 17/072 227/175.1 |
| 2012/0228358 A1* | 9/2012 | Zemlok | A61B 17/072 227/176.1 |
| 2012/0241497 A1* | 9/2012 | Mandakolathur | A61B 17/00491 227/176.1 |
| 2013/0075448 A1* | 3/2013 | Schmid | A61B 17/07207 227/176.1 |
| 2013/0119109 A1* | 5/2013 | Farascioni | A61B 17/07207 227/175.1 |
| 2013/0172929 A1 | 7/2013 | Hess et al. | |
| 2013/0277410 A1 | 10/2013 | Fernandez et al. | |
| 2014/0041191 A1 | 2/2014 | Knodel | |
| 2014/0175146 A1 | 6/2014 | Knodel | |
| 2015/0297236 A1* | 10/2015 | Harris | A61B 17/0644 227/176.1 |
| 2015/0359536 A1* | 12/2015 | Cropper | A61B 17/07207 227/177.1 |
| 2016/0058439 A1* | 3/2016 | Shelton, IV | A61B 17/068 227/176.1 |
| 2016/0058441 A1* | 3/2016 | Morgan | A61B 17/0644 606/219 |
| 2016/0058446 A1* | 3/2016 | Shelton, IV | A61B 17/0644 227/176.1 |
| 2016/0058447 A1* | 3/2016 | Posada | A61B 17/105 227/177.1 |
| 2017/0119402 A1* | 5/2017 | Heinemann | A61B 17/1608 |

FOREIGN PATENT DOCUMENTS

| | | |
|---|---|---|
| WO | WO-9915086 A1 | 4/1999 |
| WO | WO-2004032762 A1 | 4/2004 |
| WO | WO-2009038550 A1 | 3/2009 |
| WO | WO-2012015795 A1 | 2/2012 |

OTHER PUBLICATIONS

"MicroCutter XCHANGE™ 30." Instructions for Use. (2014).
"MicroCutter XCHANGE® 30 Videos." Cardica. Web. May 7, 2014. http://www.cardia.com/inservice-guide.php.
"MicroCutter XCHANGE® 30: The World's First and Only Articulating 5mm Stapler." Cardica. Web. May 7, 2014. http://www.cardica.com/minimally-invasive-surgery.php.
U.S. Appl. No. 14/300,954, filed Jun. 10, 2014.

\* cited by examiner

METHODS AND DEVICES FOR ADJUSTING A TISSUE GAP OF AN END EFFECTOR OF A SURGICAL DEVICE

FIELD OF THE INVENTION

The present disclosure relates generally to adjusting a tissue gap of an end effector of a surgical device.

BACKGROUND

Minimally invasive surgical instruments are often preferred over traditional open surgical devices due to the reduced post-operative recovery time and minimal scarring associated with minimally invasive procedures. Laparoscopic surgery is one type of minimally invasive surgery (MIS) procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. Endoscopic surgery is another type of MIS procedure in which elongate flexible shafts are introduced into the body through a natural orifice.

Due to the benefits associated with minimally invasive surgeries, significant efforts have gone into developing a range of endoscopic and laparoscopic surgical instruments that are suitable for precise placement of a distal end effector at a desired surgical site. These distal end effectors engage the tissue in a number of ways to achieve a diagnostic or therapeutic effect (e.g., grasper, cutter, stapler, clip applier, access device, drug/gene therapy delivery device, and energy device using ultrasound, radiofrequency, laser, etc.).

For example, staplers including end effectors for grasping tissue have been developed which secure tissue between two jaws. Staples contained in one of the jaws can be driven into the grasped tissue and deformed to hold the tissue by impinging on the other jaw. The staples can form a predetermined pattern (e.g., one or more lines of staples) based upon the configuration of the staples in the one of the jaws. The stapler can be a linear stapler, in which the predetermined pattern includes one or more longitudinal lines of staples. Though staplers can be effective to grasp and staple tissue, it can be difficult to grasp and/or staple the tissue based on a variety of factors, such as a size and/or shape of the staple, a thickness and/or toughness of the tissue, etc.

Some staplers can be refilled after firing staples. In some staplers, the staples can be contained in a cartridge which can be removable from the stapler's jaw to allow the stapler to be refilled with staples contained in another cartridge inserted into the jaw. However, this refilling of cartridges can be difficult since the cartridges can be relatively small and accordingly difficult to manipulate and/or properly secure within the jaw. Refilling a stapler with a new cartridge can thus be time consuming and/or can result in an improperly loaded cartridge that can misfire staples or otherwise function improperly during use on a patient.

Accordingly, there remains a need for improved methods and devices for stapling tissue.

SUMMARY

According to one aspect of the method, when the pin in the first position it prevents pivotal movement of the anvil and the cartridge jaw relative to one another. In another aspect, when the pin in the first position it prevents actuation of a firing mechanism to eject a plurality of staples from the staple cartridge. According to the method when the cartridge is positioned within the channel of the cartridge jaw it sets a clamp gap between the cartridge jaw and the anvil.

A surgical fastening device comprises an elongate shaft, an end effector coupled to a distal end of the elongate shaft, and a cartridge removably seated within a channel in the cartridge jaw of the end effector. The end effector includes a cartridge jaw and an anvil pivotally coupled to one another and movable between an open position and a closed position in which tissue can be engaged therebetween, wherein a distance between a proximal end of each of the cartridge jaw and the anvil is adjustable. Further, the cartridge includes an anvil coupling member slidably disposed therein and configured to couple to a drive shaft extending through the elongate shaft for advancing the anvil coupling member distally through the end effector. In one aspect a proximal end of the anvil coupling member includes a feature formed therein for receiving a corresponding feature formed in a distal end of the drive shaft. In another aspect the anvil coupling member engages and distally advances through a slot formed in the anvil, and a distal end of the anvil includes an opening formed therein for releasing the anvil coupling member to allow the anvil to be moved to an open position away from the cartridge jaw.

The anvil coupling member can include a knife formed on a distal-facing surface thereof for cutting tissue engaged between the cartridge jaw and the anvil. In addition the drive shaft can include a mating element formed on a distal end thereof that engages and slides within a slot formed in the cartridge jaw. In one aspect the anvil coupling member is configured to pivot away from the anvil when the anvil coupling member is positioned at a distal-most end of the anvil.

A staple cartridge is provided that comprises a cartridge housing, a plurality of staples disposed within the cartridge housing, wherein the plurality of staples being frangibly detached to a carrier, and an anvil coupling member slidably disposed within a track formed in the cartridge. The anvil coupling member includes a proximal portion having an engagement feature on a proximal-facing surface thereof for mating with a drive shaft, and the anvil coupling member includes a distal portion pivotally coupled to the proximal portion.

The anvil coupling member can include a knife on a distal-facing surface thereof. Further, the engagement feature can comprise a detent formed in the proximal-facing surface of the anvil coupling member. In one aspect the proximal portion includes a pin extending therethrough and protruding from lateral sides thereof. The pin is configured to engage and slide within a slot formed in an anvil of an end effector of a stapling device.

A method for stapling tissue is also provided. The method comprises positioning a cartridge having a plurality of staples and an anvil coupling member disposed therein within a first jaw of an end effector of a surgical stapler. The method also includes engaging tissue between the first jaw and a second jaw of the end effector, and advancing a drive shaft through the surgical stapler such that a distal end of the drive shaft abuts a proximal end of the anvil coupling member to distally advance the anvil coupling member through the end effector. The anvil coupling member has a first engagement feature that rides within a slot formed in a second jaw of the end effector, and the drive shaft has a second engagement feature that rides within a slot formed in the first jaw.

In one aspect of the method the anvil coupling member includes a knife on a distal facing surface thereof that cuts the tissue engaged between the first and second jaws. Another feature of the method is that the first engagement feature moves out of and releases the second jaw when the anvil coupling member reaches a distal-most end of the second jaw. Further, the anvil coupling member pivots away from the second jaw when the anvil coupling member is fully distally advanced through the second jaw, and the method further comprises opening the first and second jaws to release the tissue.

BRIEF DESCRIPTION OF THE DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Figure 1:
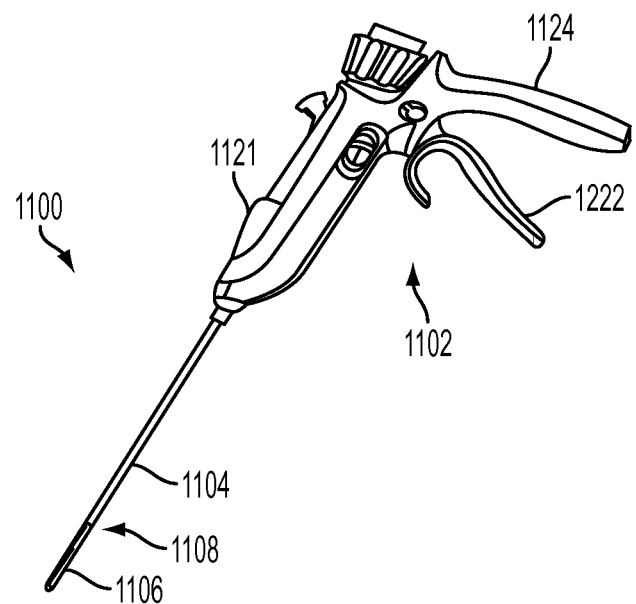
FIG. 1 is a perspective view of one embodiment of a surgical device configured to apply fasteners to tissue and including an end effector, the end effector being in a closed position.

FIG. 1 illustrates one embodiment of a surgical device 1100 that can be configured to apply staples to tissue. The device 1100 in this illustrated embodiment includes a linear stapler configured to apply linear rows of staples. Other embodiments of surgical devices that can be configured to apply staples to tissue are described in U.S. Pat. No. 5,465,895 entitled "Surgical Stapler Instrument" filed Feb. 3, 1994, U.S. Pat. No. 7,000,818 entitled "Surgical Stapling Instrument Having Separate Distinct Closing And Firing Systems" filed May 20, 2003, U.S. Pat. No. 7,669,746 entitled "Staple Cartridges For Forming Staples Having Differing Formed Staple Heights" filed on Aug. 31, 2005, and U.S. Pat. Pub. No. 2014/0175146 entitled "Microcutter Stapling Apparatus Clamp And Deploy Mechanisms Systems And Methods" filed Dec. 19, 2013, which are hereby incorporated by reference in their entireties.

Figure 2:
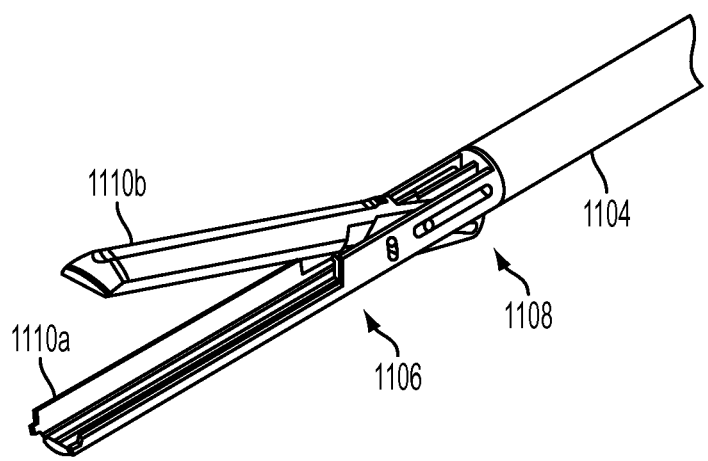
FIG. 2 is a perspective view of the end effector of FIG. 1 in an open position.
Figure 3:
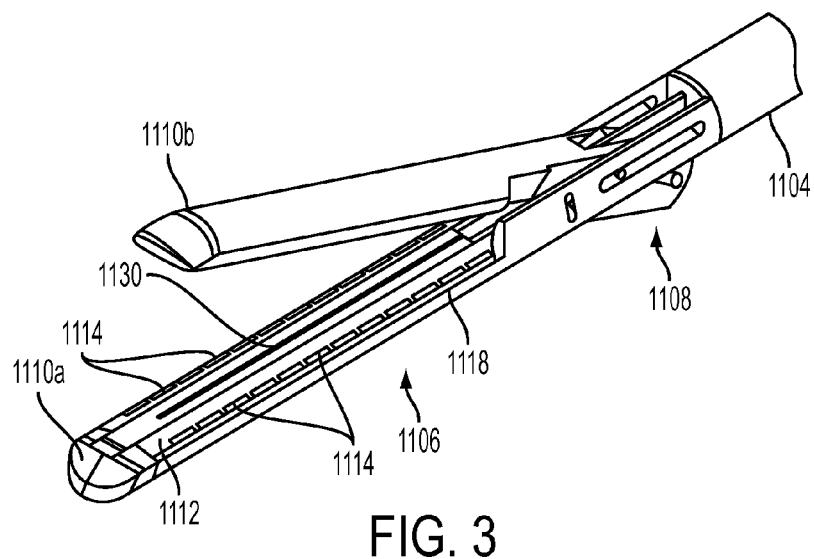
FIG. 3 is a perspective view of the end effector of FIG. 2 with one embodiment of a cartridge removably coupled thereto.

Referring again to FIG. 1, the device 1100 can include a proximal handle portion 1102 having an elongate shaft 1104 extending distally therefrom. As also shown in FIG. 2 and FIG. 3, the shaft 1104 can have an end effector 1106 coupled to a distal end thereof. The end effector 1106 can be coupled to the shaft 1104 at a pivot joint 1108. A proximal end of the end effector 1106 can be pivotally coupled to the joint 1108 at a distal end of the shaft 1104. The end effector 1106 in this illustrated embodiment includes a tissue grasper having a pair of opposed first and second jaws 1110a, 1110b configured to move between open and closed positions. The first jaw is also referred to herein as a "bottom jaw" and a "cartridge jaw," and the second jaw is also referred to herein as an "upper jaw" and an "anvil." As discussed further below, the handle portion 1102 can be configured to be manipulated to effect the opening and closing of the opposed jaws 1110a, 1110b, e.g., movement of one or both the jaws 1110a, 1110b about the pivot joint 1108, and the handle portion 1102 can be configured to be manipulated to effect the firing of staples (not shown) from a one of the jaws 1110a, 1110b, e.g., a bottom or cartridge one of the jaws 1110a. The staple firing can be independent of the opening and closing of the jaws 1110a, 1110b.

The handle portion 1102 can have a variety of sizes, shapes, and configurations. The handle portion 1102 can include a main housing 1121, which can house a variety of elements therein and can have some elements accessible outside thereof, such as a movable trigger 1122 and a stationary handle 1124. The movable trigger 1122 can be configured to be manually manipulated to move the movable trigger 1122 relative to the stationary handle 1124 so as to, e.g., effect closing of the jaws 1110a, 1110b.

The shaft 1104 can have a variety of sizes, shapes, and configurations. In an exemplary embodiment, the shaft 1104 can be rigid, e.g., made from a generally non-bendable material such as a metal (e.g., stainless steel, titanium, etc.) or a hard polymer. In other embodiments, the shaft 1104 can be configured to bend, such as being made from a generally flexible material, by including one or more articulation regions, etc. The shaft 1104 can have any longitudinal length, although in an exemplary embodiment it can be long enough to allow the handle portion 1102 to be manipulated outside a patient's body while the shaft 1104 extends through an opening in the body with the end effector 1106 disposed within a body cavity. In this way, the end effector 1106 can be easily manipulated when the device 1100 is in use during a surgical procedure. The shaft 1104 can have any diameter. For example, the shaft's diameter can be less than or equal to about 10 mm, e.g., less than or equal to about 7 mm, less than or equal to about 5 mm, etc., which can allow for insertion of the shaft 1104 through an minimally invasive access device, e.g., a trocar, a cannula, a multiport access device, etc., such as during a laparoscopic surgical procedure. The end effector 1106 coupled to the shaft's distal end can have a diameter equal to or less than the shaft's diameter, at least when the jaws 1110a, 1110b are in the closed position, which can facilitate insertion of the device's distal portion into a patient's body.

The end effector 1106 can have a variety of sizes, shapes, and configurations. In an exemplary embodiment, the end effector 1106 can be rigid. As shown in FIG. 2 and FIG. 3, the end effector 1106 including the first and second jaws 1110a, 1110b can be disposed at a distal end of the surgical device 1100. As in this illustrated embodiment, when the jaws 1110a, 1110b move between the open and closed positions, the second jaw 1110b can be configured to remain stationary relative to the shaft 1104, and the first jaw 1110a can be configured to move relative to the shaft 1104 and the second jaw 1110b by pivoting at the pivot joint 1108.

Figure 4:
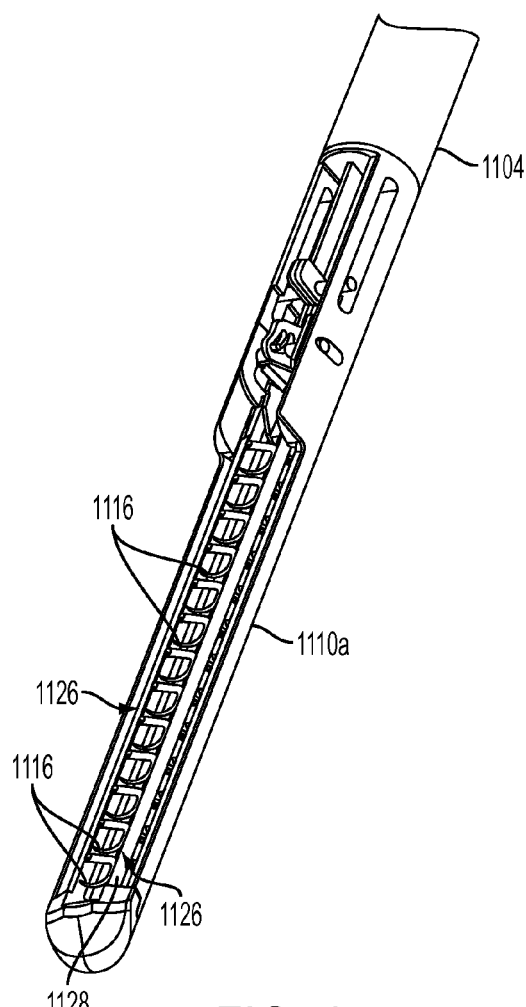
FIG. 4 is a perspective, partially cross-sectional view of the end effector and the cartridge of FIG. 3.

The end effector 1106 can be configured to releasably and replaceably seat a cartridge 1112 therein, as shown in FIG. 3 and FIG. 4. In this way, when the staples have been fired from the cartridge 1112, the cartridge 1112 can be removed from the second jaw 1110b and, optionally, replaced with another cartridge having another plurality of staples disposed therein. FIG. 2 shows the end effector 1106 without the cartridge 1112 seated therein. The end effector 1106 can be configured to receive the cartridge 1112 in the first jaw 1110a thereof, e.g., in a channel formed in the first jaw 1110a. The first jaw 1110a can be configured to seat cartridges of different sizes, thereby facilitating versatility of the device 1100.

Figure 5:
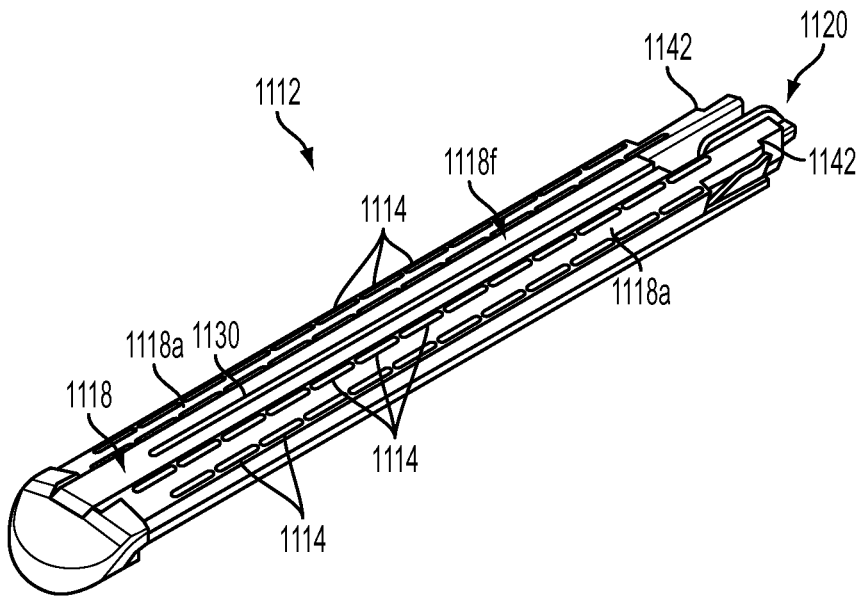
FIG. 5 is a perspective view of the cartridge of FIG. 3.
Figure 6:
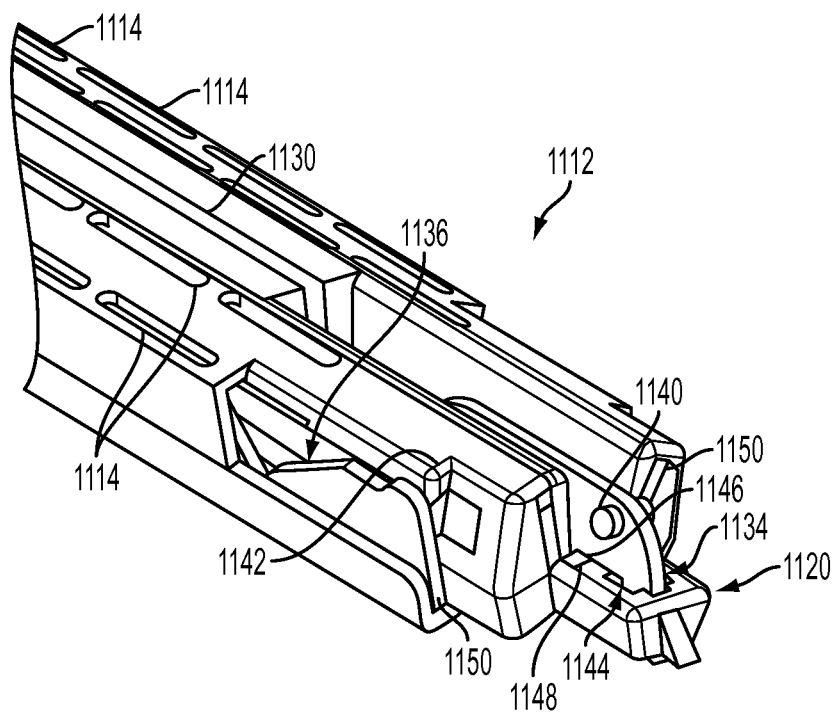
FIG. 6 is another perspective view of the cartridge of FIG. 3.
Figure 7:
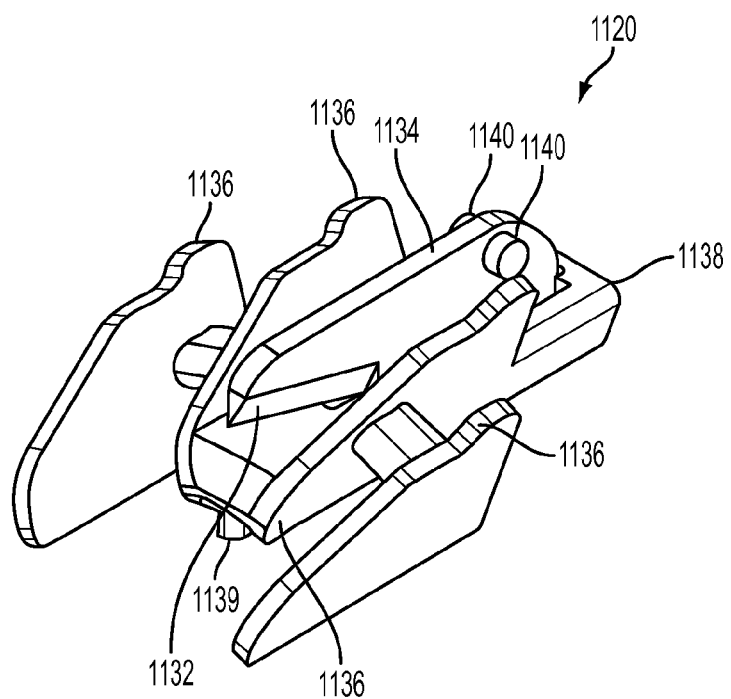
FIG. 7 is a perspective view of a sled of the cartridge of FIG. 3, the sled including a cutting element, and the cutting element being in a first position.
Figure 8:
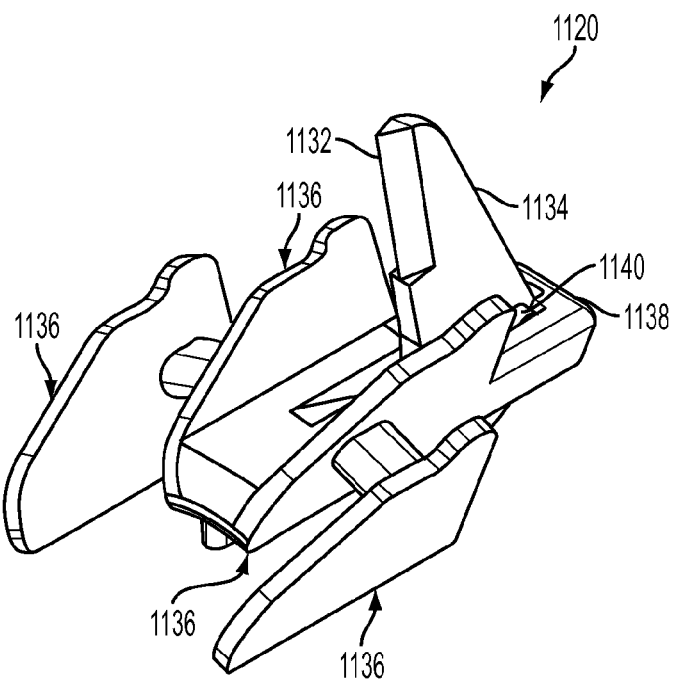
FIG. 8 is a perspective view of the sled of FIG. 7 with the cutting element in a second position that is different from the first position.

The cartridge 1112 can have a variety of sizes, shapes, and configurations, as will be appreciated by a person skilled in the art. As shown in FIG. 4, FIG. 5, and FIG. 6, the cartridge 1112 can include a sled 1120 and can have a plurality of staples 1116 disposed therein. The sled 1120 is also illustrated in FIG. 7 and FIG. 8. The cartridge 1112 can include a plurality openings 1114 formed in a tissue engaging surface 1118 thereof, as shown in FIG. 3, FIG. 5, and FIG. 6. The staples 1116 disposed in the cartridge 1112 can be configured to be ejected from the cartridge 1112 through the openings 1114, e.g., one staple 1116 out of each opening 1114 (as in this illustrated embodiment), two staples out of each opening 1114, etc. The openings 1114 can define staple-receiving recesses of the cartridge 1112 in which the staples 1116 are seated prior to being ejected from the cartridge 1112.

The staples 1116 can have a variety of sizes, shapes, and configurations. In this illustrated embodiment, the staples 1116 each have a D-shape and include a first leg that is substantially straight and a second leg that is curved. A person skilled in the art will appreciate that the first leg may not be precisely straight, e.g., due to manufacturing tolerances, but nevertheless be considered to be substantially straight. Each of the staples 1116 can be configured to be plastically deformable such that the staples 1116 can each be configured to change shape, such as when the staple 1116 is pressed against a tissue engaging surface (not shown) of the first jaw 1110a that faces the tissue engaging surface 1118 of the second jaw 1110b, while remaining a single unit, e.g., without either of the first and second legs breaking. A gap of space can exist between a terminal end of the first leg and a terminal end of the second leg. In other words, the "D" shape can have a gap therein. The gap of space can facilitate plastic deformation of the staple 1116.

The staples 1116 can each be frangibly attached to a carrier 1126, also referred to herein as a "carrier strip," disposed within the cartridge 1112. The staples 1116 can be frangibly attached to the carrier 1126 by, e.g., being stamped together with the carrier 1126 such that the staples 1116 and the carrier 1126 forms a single piece. The staples 1116 can each be configured to detach from the carrier 1126 when fired from the cartridge 1112. In some embodiments, some or all of the staples 1116 can be frangibly attached to another element, such as another element disposed within the cartridge 1112, an inner surface of the cartridge 1112, the tissue-engaging surface 1118 of the cartridge 1112, etc. The carrier 1126 can be fixedly attached to an upper surface of one or more rails 1128 defined by the cartridge 1112. The carrier 1126 can be configured to remain stationary relative to the cartridge 1112.

As shown in FIG. 3, FIG. 5, and FIG. 6, the cartridge 1112 can have a longitudinal slot 1130 formed therein. The longitudinal slot 1130 can extend along a substantially flat central portion 1118f of the tissue-engaging surface 1118. The slot 1130 can be configured to have a cutting element such as a knife (not shown) extend therethrough so as to be configured to cut tissue engaged by the tissue-engaging surface 1118, as discussed further below. The openings 1114 can be formed in angled portions 1118a of the tissue-engaging surface 1118 on both sides of the slot 1130, as shown in FIG. 3, FIG. 5, and FIG. 6. In some embodiments, the tissue-engaging surface 1118 can be substantially flat, e.g., not have angled portions, while in other embodiments, the tissue-engaging surface 1118 can be angled, e.g., not have any substantially flat portions.

As shown in FIG. 5 and FIG. 6, the cartridge 1112 can include a gap-setting feature 1142 configured to set of gap of space between the first and second jaws 1110a, 1110b when the jaws 1110a, 1110b are closed and the cartridge 1112 is seated in the second jaw 1110b. In this way, the gap-setting feature 1142 can be configured to define a minimum distance between the facing tissue-engaging surfaces of the first and second jaws 1110a, 1110b. The gap-setting feature 1142 can have a variety of sizes, shapes, and configurations. As in this illustrated embodiment, the gap-setting feature 1142 can include an indentation inward toward a lateral center of the cartridge 1112, where a portion of a lateral edge of the cartridge 1112 immediately proximal to the gap-setting feature 1142 is located laterally inward relative to a portion of a lateral edge of the cartridge 1112 located immediately distal to the gap-setting feature 1142.

The sled 1120 of the cartridge 1112 can have a variety of sizes, shapes, and configurations. The sled 1120 can be configured to translate longitudinally along the cartridge 1112 to cause deployment of the staples 1116 therefrom and to cause tissue engaged by the end effector 1106 to be cut with the cutting element extending through the slot 1130. The staples 1116 can be arranged longitudinally in the cartridge 1112, as shown in FIG. 4, and the sled 1120 can be configured to sequentially engage the longitudinally arranged staples 1116 as the sled 1120 translates longitudinally. As illustrated in FIG. 7 and FIG. 8, the sled 1120 can include a plurality of wedges 1136 and can include a cutting element 1134, which in this illustrated embodiment includes a knife with a blade 1132. The sled 1120 in this illustrated embodiment includes four wedges 1136 but the sled 1120 can include another number of wedges 1136 as appropriate for the arrangement of the staples 1116 in the cartridge 1112. Each of the wedges 1136 can have a shape configured to cause the staples 1116 contacted by that wedge 1136 to move upward toward the second jaw 1110b through the openings 1114 and deform against the second jaw 1110b. As shown in FIG. 6, the cartridge 1112 can include a plurality of longitudinal slots 1150 formed therein, each of the slots 1150 being configured to slidably receive one of the wedges 1136 therein. The slots 1150 can facilitate consistent, straight movement of the wedges 1136 through the cartridge 1112 to help ensure proper engagement of the wedges 1136 with the staples 1116.

Each of the wedges 1136 can be attached to a base 1138 of the sled 1120 and can be in a fixed position relative thereto. The base 1138 can have a guide element 1139 extending generally downward therefrom. The guide element 1139 can be configured to slide within a channel formed in the cartridge 1112 that includes the sled 1120. The cutting element 1134 can also be attached to the base 1138, but the cutting element 1134 can be configured to move relative to the base 1138. The cutting element 1134 can be substantially laterally centered in the base 1138, which can facilitate substantially central positioning of the cutting element 1134 relative to tissue engaged by the end effector 1106.

The cutting element 1134 can be configured to be movable relative to a remainder of the sled 1120 between a first position, shown in FIG. 7, and a second position, shown in FIG. 6 and FIG. 8. The first position can be an initial position of the cutting element 1134. In the first position, also referred to herein as a "stowed position," the blade 1132 can be generally obscured, e.g., oriented generally downward as shown in the embodiment of FIG. 4, FIG. 5, FIG. 6, and FIG. 7, which can help prevent the blade 1132 from inadvertent cutting, such as accidentally cutting a user of the device 1100 during seating of the cartridge 1120 within the end effector 1104 and/or premature cutting of tissue engaged by the end effector 1104. The base 1138 can have a cavity 1144 formed therein, as shown in FIG. 6, which can be configured to seat the cutting element 1134 at least partially therein when the cutting element 1134 is in the first position. In the second position, also referred to herein as an "upright position," the blade 1132 can be generally unobscured and facing a distal direction as shown in the embodiment of FIG. 6 and FIG. 8, which can allow the blade 1132 to extend through the slot 1130 and cut tissue engaged by the end effector 1106.

The sled 1120 can include a pivot member 1140 configured to facilitate movement of the cutting element 1134 relative to the remainder of the sled 1120. The pivot member 1140 can have a variety of sizes, shapes, and configurations. The pivot member 1140 can be attached to the cutting element 1134 such that engagement of the pivot member 1140 can cause the cutting element 1134 to pivot about a pivot point so as to move relative to the remainder of the sled. As in this illustrated embodiment the pivot member 1140 can include two separate pins extending laterally from opposite sides of the cutting element 1134. In other embodiments, the pivot member 1140 can include a single pin extending through the cutting element 1134 to extend laterally from opposite sides therefrom, a single pin extending laterally from one side of the cutting element 1134, etc. At the pivot point, the sled 1120 can include a pivot axle 1146 extending laterally from the cutting element 1134, and can include an axle cavity 1148 formed in the base 1138 and configured to receive the pivot axle 1146 therein.

The surgical devices described herein can be used in a variety of surgical procedures. In an exemplary embodiment, the procedure can be a minimally invasive procedure in which the surgical device can be advanced into a body of a patient through a relatively small opening in the patient. In a minimally invasive surgical procedure, one or more introducer devices (not shown), e.g., a cannula, a trocar, etc., can be advanced through an opening in the patient to provide access to a surgical site. A person skilled in the art will appreciate that one or more viewing devices, e.g., a scoping device such as an endoscope, can be advanced into the body through the incision or through another opening, e.g., another incision or a natural orifice, to provide visualization of the surgical site from outside the body. As will be appreciated by a person skilled in the art, the surgical device can be advanced into the patient's body in a variety of ways, such as by being inserted transorally therein, inserted through an introducer device, inserted through a scoping device, inserted directly through an incision, etc. Although the following embodiment of use of a surgical device in a surgical procedure is described with respect to the device 1100 of FIG. 1, any of the surgical devices described herein can be similarly used.

The surgical devices described herein can have any one or more variations to facilitate effective use of the device. Examples of such variations are described further below.

In some embodiments, a surgical device such as the above-mentioned surgical device 1100 can be configured to have an adjustable gap of space between a cartridge jaw and an anvil of the device's end effector when the end effector is in a closed position. In general, the end effector, e.g., the cartridge jaw, can be configured to removably couple to a cartridge, as discussed herein. The cartridge can be configured to define the gap of space between the cartridge jaw and the anvil when the end effector is in a closed position. In other words, the gap of space can be a function of the cartridge. The gap of space can be a minimum distance between facing tissue-engaging surfaces of the cartridge jaw and the anvil. The end effector can thus be configured to selectively accommodate tissues of different thicknesses since the end effector's tissue gap can be different based upon the specific cartridge loaded therein. In an exemplary embodiment, the cartridge can include an anvil coupling member configured to define the gap of space so as to provide a minimum distance between the facing tissue-engaging surfaces of the cartridge jaw and the anvil when the end effector is in the closed position. The anvil coupling member can form a partial portion of an I-beam configured to translate longitudinally along the end effector, as discussed herein. The anvil coupling member forming a partial portion of the I-beam can allow the I-beam to be appropriately sized for the tissue gap defined by the anvil coupling member such that the I-beam can properly translate along the cartridge, e.g., via a foot of the I-beam," and along the anvil, e.g., via a guide pin of the I-beam. The anvil coupling member forming a partial portion of the I-beam can result in the I-beam being different in the surgical device as a function of the cartridge seated in the end effector. The I-beam can thus be configured to be adjustable so as to correspond to the adjustable gap of space between the end effector's jaws.

A surgical device can be configured to have an adjustable gap of space between a cartridge jaw and an anvil of the device's end effector when the end effector is in a closed position in a variety of ways. In the embodiments described below, staples are used as examples of fasteners, but as will be appreciated by a person skilled in the art, other types of fasteners can be similarly configured and used.

In some embodiments, an anvil coupling member can be in the form of a partial portion of an I-beam. As discussed herein, an I-beam can be configured to translate longitudinally along an end effector to fire fasteners from a cartridge seated in the end effector. The I-beam can be configured to contact the end effector's bottom jaw with a first portion thereof, e.g., with a foot thereof, and the end effector's anvil with a second portion, e.g., with a guide pin thereof. The anvil coupling member can include the second portion of the I-beam configured to contact the anvil such that the cartridge being loaded into the bottom jaw of the end effector can define a gap of space between the cartridge's tissue-engaging surface and the anvil's tissue-engaging surface.

Figure 9:
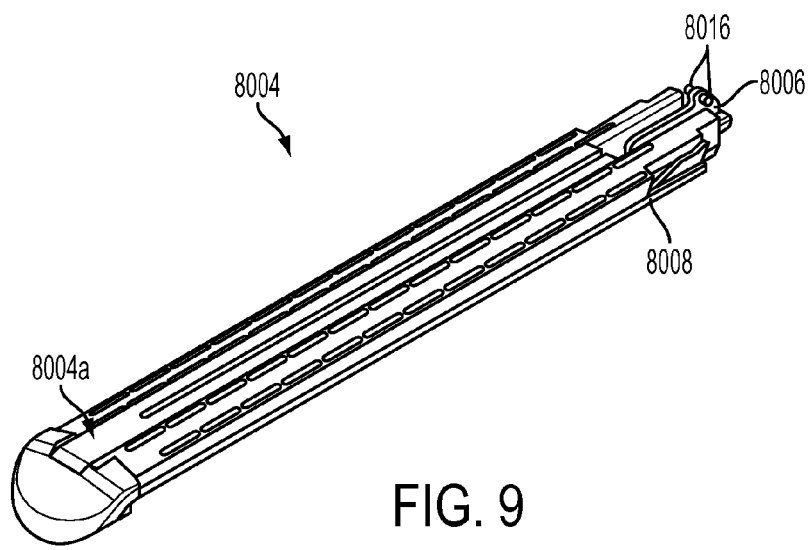
FIG. 9 is a perspective view of one embodiment of a cartridge including an anvil coupling member.
Figure 10:
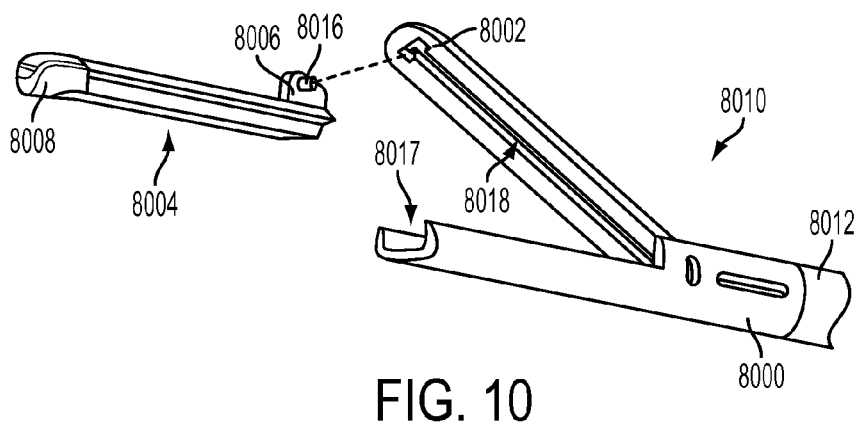
FIG. 10 is a perspective exploded view of the cartridge of FIG. 9 and a distal portion of a surgical device configured to releasably and replaceable seat the cartridge.
Figure 11:
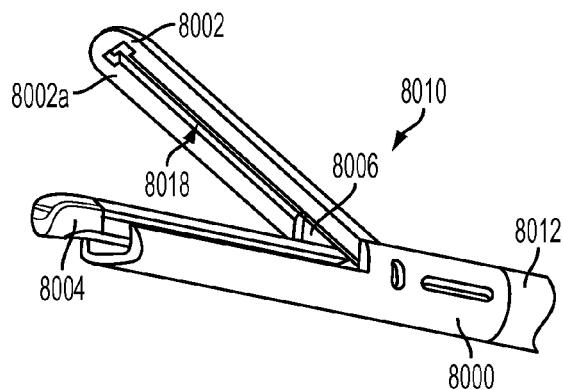
FIG. 11 is a perspective view of the cartridge and the distal portion of the surgical device of FIG. 10, the cartridge partially seated within the distal portion.

FIG. 9, FIG. 10, and FIG. 11 illustrate one embodiment of a cartridge 8004 that includes an anvil coupling member 8006 coupled thereto. The anvil coupling member 8006 can be configured to move relative to a housing 8008 of the cartridge 8004 that had fasteners (not shown) disposed therein, as discussed further below. In general, the cartridge 8004 can be configured to be removably coupled to an end effector 8010 coupled to a distal end of an elongate shaft 8012, such as by being releasably and replaceably seated in a channel 8017 formed in a bottom jaw 8000 of the end effector 8010. The cartridge 8004 can also be configured to be releasably and replaceably seated in a slot 8018 formed in an anvil 8002 of the end effector 8010, such as by coupling the anvil coupling member 8006 thereto. The anvil coupling member 8006 can be configured to slidably move within the slot 8018 as part of an I-beam 8014, shown in FIG. 12.

The anvil coupling member 8006 can have a variety of sizes, shapes, and configurations. As in this illustrated embodiment, the anvil coupling member 8006 can include a protrusion extending upwardly from the cartridge 8004 so as to extend above a tissue-engaging surface 8000a of the cartridge 8004. This protrusion can includes a guide pin 8016 extending laterally from the protrusion and being configured to slidably move with the anvil's slot 8018.

Figure 12:
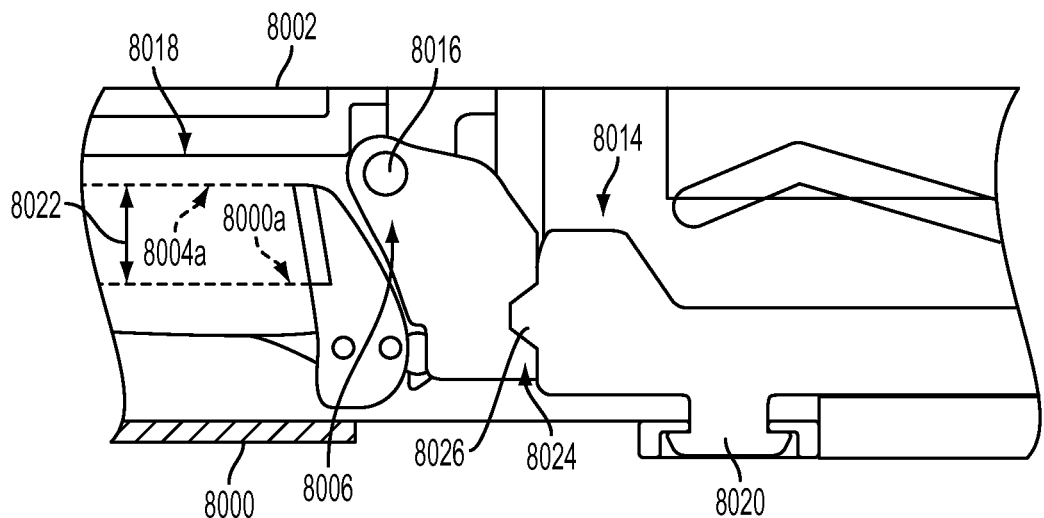
FIG. 12 is a side cross-sectional view of the distal portion of the device of FIG. 11, the cartridge being fully seated therein.

As in this illustrated embodiment, the anvil coupling member 8006 can include a proximal portion of the I-beam 8014. The anvil coupling member 8006 can include a first coupling element 8024 configured to removably couple to a second coupling element 8026 of a remainder of the I-beam 8014, e.g., a distal portion of the I-beam 8014. The distal portion of the I-beam 8014 in this illustrated embodiment includes a foot 8020 of the I-beam 8014, but in other embodiments, the anvil coupling member 8006 can include the foot 8020. As in this illustrated embodiment, the first coupling element 8024 includes at least one depression formed in a proximal side of the anvil coupling member 8006, and the second coupling element 8026 can include at least one protrusion formed in a distal side of the remainder of the I-beam 8014. In other embodiments, the first coupling element can include at least one protrusion, and the second coupling element can include at least one depression. When the cartridge 8004 is fully seated in the cartridge jaw 8000, as shown in FIG. 12, the first and second coupling elements can be coupled together so as to allow the I-beam 8014 include the anvil coupling member 8006 and the remainder of the I-beam 8014 to move as a single unit through the end effector 8004.

The anvil coupling member 8006 can be configured to define a distance 8022 between the tissue-engaging surface 8004a of the cartridge 8004 and a tissue-engaging surface 8002a of the anvil 8002. As shown in FIG. 12, a height of the anvil coupling member 8006, can define a distance that the anvil coupling member 8006 extends above the cartridge's tissue engaging surface 8004a and can define how far away the anvil 8002 can be from the bottom jaw 8000 when the end effector 8010 is in the closed position based on a location of the guide pin 8016 on the anvil coupling member 8006. The anvil coupling member 8006 can thus be configured to help ensure that the guide pin 8016 can slide within the slot 8018 when the end effector 8010 is in the closed position, thereby allowing for firing of the fasteners.

As shown in FIG. 9 and FIG. 10, the cartridge 8004 can be configured to be advanced into the channel 8017 of the bottom jaw 8000 simultaneously with the guide pin 8016 being advanced in a proximal direction into the slot 8018 of the anvil 8002. The guide pin 8016 can thus be properly seated within the slot 8018 when the cartridge 8004 is fully seated in the bottom jaw 8000.

Figure 13:
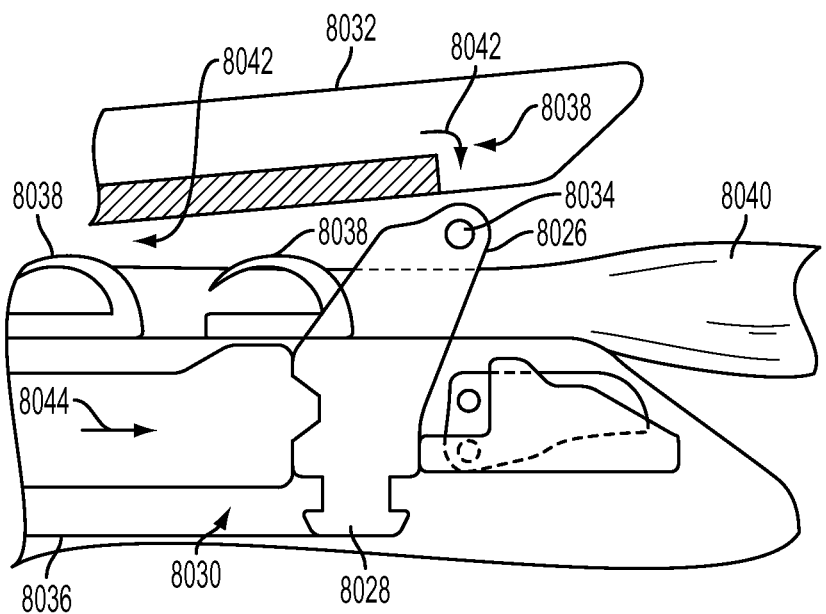
FIG. 13 is a side cross-sectional view of another embodiment of a cartridge including an anvil coupling member.

FIG. 13 illustrates an alternate embodiment of an anvil coupling member 8026 that can be configured and used similar to the anvil coupling member 8006 of FIG. 9. The anvil coupling member 8026 in this illustrated embodiment includes a foot 8028 of an I-beam 8030 of which the anvil coupling member 8026 can form a proximal portion thereof.

As in this illustrated embodiment, the I-beam 8030 can be configured to be automatically released from an anvil 8032 such that the I-beam 8030 need not be retracted after advancing through the anvil 8032 and a cartridge jaw 8036 coupled thereto so as to fire fasteners 8038 into tissue 8040 clamped in a tissue gap 8042 between the anvil 8032 and the cartridge jaw 8036. The I-beam 8030 is configured to advance in a distal direction 8044 to fire the fasteners 8038 in this illustrated embodiment. The anvil 8032 can include an opening 8038 adjacent a distal end thereof configured to release the anvil coupling member 8026, e.g., a guide pin 8034 thereof, therefrom. The anvil coupling member 8026, and hence the I-beam 8030, can be configured to be automatically released 8042 from the anvil 8032 by the guide pin 8034 passing out of the opening 8038, which can be in communication with a slot in the anvil 8032 through which the guide pin 8034 can translate. The release of the anvil coupling member 8026, and hence the I-beam 8030, from the anvil 8032 can allow the anvil 8032 to open.

In some embodiments, a shim of a cartridge configured to be removably coupled to a bottom jaw of an end effector of a surgical device can be configured to define a gap of space between the bottom jaw and an anvil coupled thereto. In general, a size of the shim can define the gap of space. The larger the shim, the smaller the gap of space.

Figure 14:
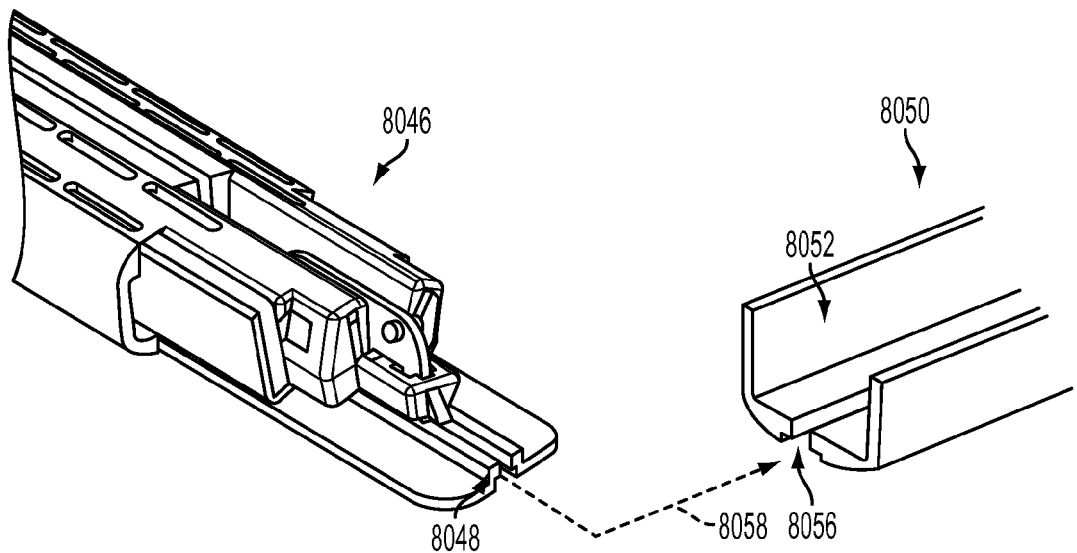
FIG. 14 is a perspective exploded view of one embodiment of a cartridge including a shim and a cartridge jaw configured to releasably and replaceably seat the cartridge therein.
Figure 15:
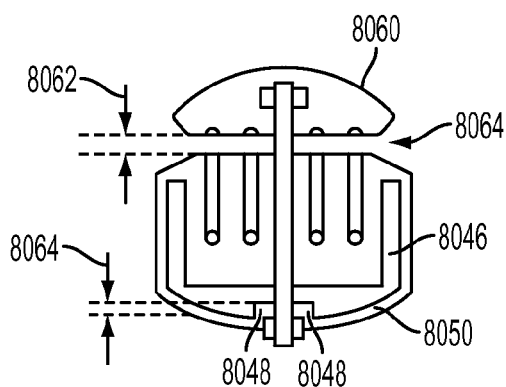
FIG. 15 is a side cross-sectional view of the cartridge of FIG. 14 seated in the cartridge jaw, the cartridge jaw being coupled to an anvil.

FIG. 14 and FIG. 15 illustrate one embodiment of a cartridge 8046 that includes a shim 8048. The cartridge 8046 can be configured to removably coupled to a cartridge jaw 8050 by being seated in a channel 8052 formed therein. The shim 8048 can have a variety of sizes, shapes, and configurations. As in this illustrated embodiment, the shim 8048 can include an upwardly extending protrusion that can be formed on a bottom inner surface of the cartridge 8046. The shim 8048 can extend along a longitudinal length of the cartridge 8046

The cartridge jaw 8050 can include a receiving slot 8054 formed therein that can be configured to slidably receive the shim 8048 therein. The cartridge 8046 can be configured to be seated within the channel 8052 by sliding the cartridge 8046 in a proximal direction 8058 with the shim 8048 sliding proximally within the slot 8054. The shim 8048 can thereby define a height 8062 of a gap of space 8064, shown in FIG. 15, between the cartridge jaw 8050 and an anvil 8060 coupled thereto. The shim 8048 extending along the cartridge's longitudinal length can help the shim 8048 define the height 8062 consistently along the end effector's longitudinal length.

Figure 16:
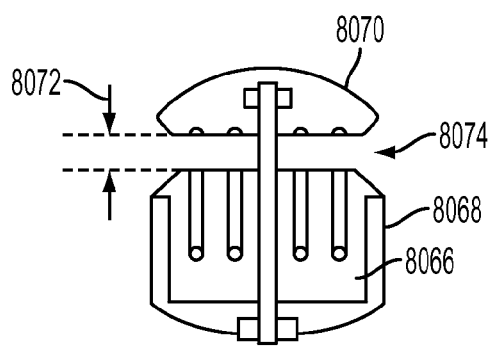
FIG. 16 is a side cross-sectional view of another embodiment of a cartridge seated in a cartridge jaw, the cartridge jaw being coupled to an anvil.

A height 8064 of the shim 8048 can define the tissue gap's height 8062. By way of comparison, FIG. 16 shows a cartridge 8066 without a shim seated in a cartridge jaw 8068 coupled to an anvil 8070. A height 8072 of a tissue gap 8074 can thus be greater than the tissue gap's height 8062 defined by the shim 8048 of FIG. 15.

Figure 17:
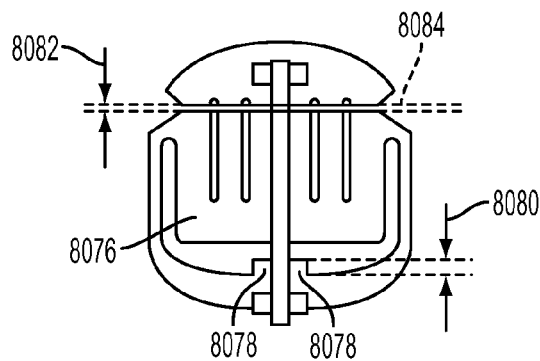
FIG. 17 is a side cross-sectional view of another embodiment of a cartridge including a shim seated in a cartridge jaw, the cartridge jaw being coupled to an anvil.

FIG. 17 illustrates another embodiment of a cartridge 8076 that includes a shim 8078. The shim 8078 can be generally configured and used similar to the shim 8048 of FIG. 14. The shim 8078 in this illustrated embodiment has a height 8080 that is greater than the height 8064 of the shim 8048 of FIG. 15. Thus, a height 8082 of a tissue gap 8084 can be less than the tissue gap's height 8062 defined by the shim 8048 of FIG. 15.

In some embodiments, a cutting element of a sled can be configured to define a gap of space between a bottom jaw and an anvil coupled thereto. As discussed herein, the sled can be part of a cartridge configured to be removably coupled to an end effector of a surgical device. The cartridge can thus be configured to define the gap of space.

Figure 18:
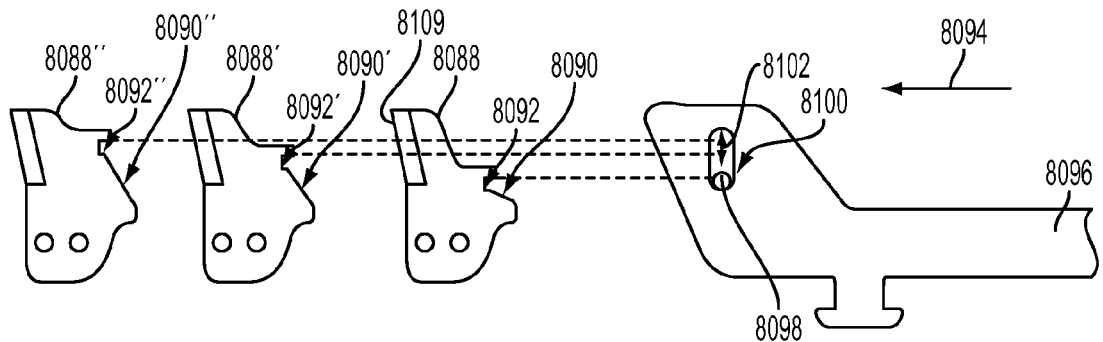
FIG. 18 is a side view of first, second, and third embodiments of a cutting element each configured to removably couple to an I-beam.

FIG. 18 illustrates one embodiment of a cutting element 8088 configured to define a gap of space (not shown) between jaws of an end effector (not shown). The cutting element 8088 can be part of a sled (not shown) of a cartridge (not shown) configured to be removably coupled to an end effector (not shown), as discussed herein. The cutting element 8088 can include an I-beam mating feature 8090 formed on a proximal side thereof, opposite to a blade 8104 formed on a distal side thereof. The I-beam mating feature can include a ramped surface 8090 that can slope upward in a distal direction 8094 toward a pin stop depression 8092 that can extend in the distal direction 8094. The I-beam mating feature 8090 can be configured to removably couple to an I-beam 8096. The I-beam 8096 can include a guide pin 8098 configured to be movable relative to a remainder of the I-beam 8096. As in the illustrated embodiment, the I-beam 8096 can include an I-beam pin slot 8100 in which the pin 8098 can be configured to slide. The pin slot 8100 can extend in an upward/downward or vertical direction 8102 that can be substantially perpendicular to the distal direction 8094. The pin 8098 can thus be configured to slide in the slot 8100 in the upward/downward direction 8102.

The pin 8098 can be configured to engage the cutting element 8088 when the cartridge including the cutting element 8088 is removably coupled to the end effector that is attached to an elongate shaft (not shown) along which the I-beam 8096 extends. The pin 8098 can be configured to engage a lower portion of the ramped surface 8090 of the cutting element 8088 and slide upward therealong until the pin 8098 reaches the depression 8092, which can cause the pin's sliding to stop. The depression 8092 can seat the pin 8098 therein. An upward/downward location of the pin 8098 can thus be defined by the cutting element 8088. The guide pin 8098 seated in the depression 8092 can be configured to slide along an anvil of the end effector. In this way, a tissue gap between the anvil and a cartridge jaw of the end effector can be defined by the cutting element 8088.

Figure 19:
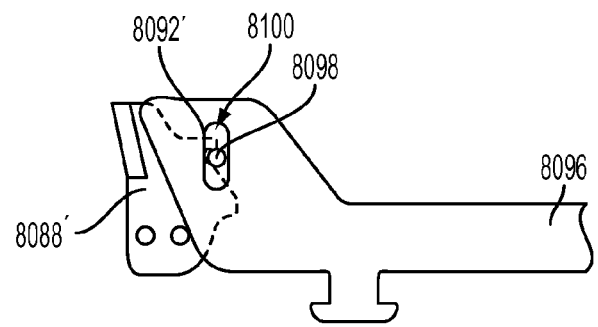
FIG. 19 is a side partially transparent view of the second cutting element of FIG. 18 coupled to the I-beam.

FIG. 18 illustrates another embodiment of a cutting element 8088' that can be configured and used similar to the cutting element 8088. FIG. 18 also illustrates another embodiment of a cutting element 8088" that can be configured and used similar to the cutting element 8088. The ramped surfaces 8090, 8090', 8090" of the cutting elements 8088, 8088', 8088", respectively, can all start at a same location in a downward direction, thereby facilitating engagement of the pin 8098 with the ramped surface of the cutting element loaded into the surgical device's end effector. The cutting element 8088' has a longer ramped surface 8090' than the cutting element 8088 such that a depression 8092' of the cutting element 8088' is located at a higher location than the depression 8092 of the cutting element 8088. The pin 8098 seated in the depression 8092', as shown in FIG. 19, can thus be up higher than the pin 8098 when seated in the lower depression 8092. The tissue gap can thus be greater when using the cutting element 8088' versus the cutting element 8088. The cutting element 8088" has a longer ramped surface 8090" than the cutting element 8088 and the other cutting element 8088' such that a depression 8092" of the cutting element 8088" is located at a higher location than the depression 8092 of the cutting element 8088 and the depression 8092' of the cutting element 8088'. The pin 8098 seated in the depression 8092" can thus be up higher than the pin 8098 when seated in either of the lower depressions 8092, 8092'. The tissue gap can thus be greater when using the cutting element 8088" versus the cutting element 8088 and versus the cutting element 8088'.

Figure 20:
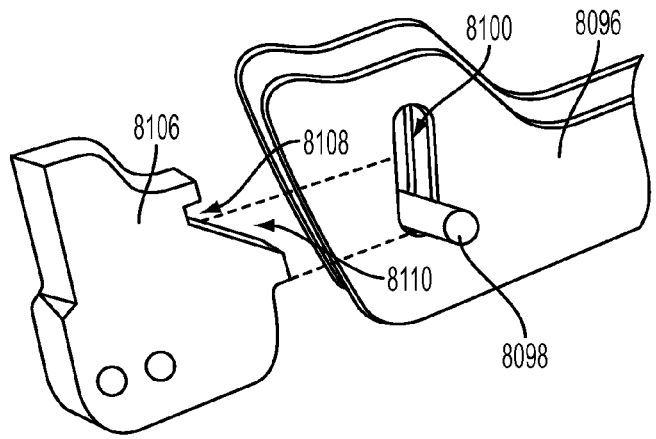
FIG. 20 is a perspective exploded view of another embodiments of a cutting element configured to removably couple to the I-beam of FIG. 18.
Figure 21:
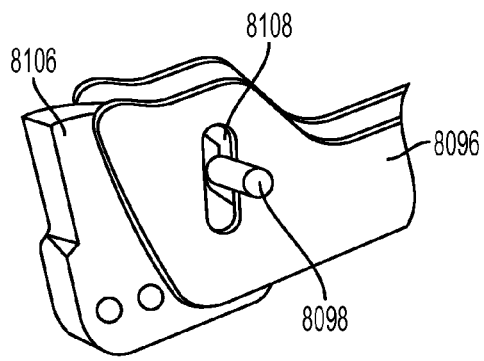
FIG. 21 is a perspective view of the cutting element of FIG. 20 removably coupled to the I-beam.

FIG. 20 and FIG. 21 illustrates another embodiment of a cutting element 8106 that can be configured and used similar to the cutting elements 8088, 8088', 8088" and removably couple to the I-beam 8096. FIG. 20 shows the I-beam 8096 disengaged from the cutting element 8106. FIG. 21 shows the pin 8098 of the I-beam 8096 seated in a depression 8108 of the cutting element's mating feature 8110.

In some embodiments of a surgical device in which a cutting element of a sled can be configured to define a gap of space between a bottom jaw and an anvil coupled thereto, the surgical device can include a push rod configured to facilitate engagement of the I-beam's pin with the cutting element. The push rod can help ensure that the pin is seated within a depression of the cutting element's mating feature, thereby helping to ensure that the anvil is at an intended position relative to the bottom jaw when the bottom jaw and the anvil are closed. The push rod can help hold the pin within the depression, which can help prevent the pin from shifting position relative to the cutting element. The tissue gap can thus be less likely to change once the pin is seated in the depression.

Figure 22:
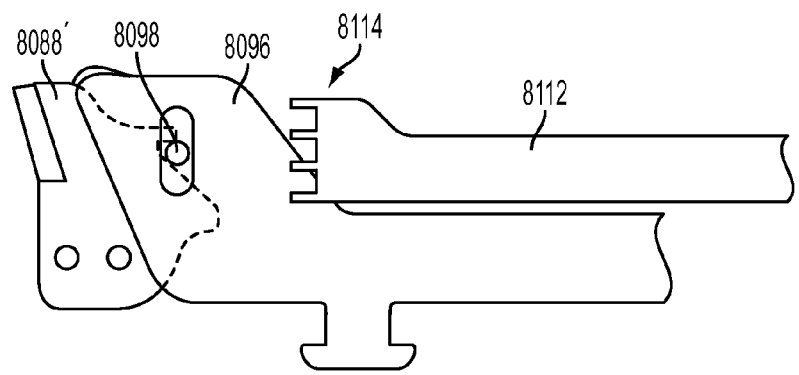
FIG. 22 is a side partially transparent view of the second cutting element and I-beam of FIG. 19 and one embodiment of a push rod.
Figure 23:
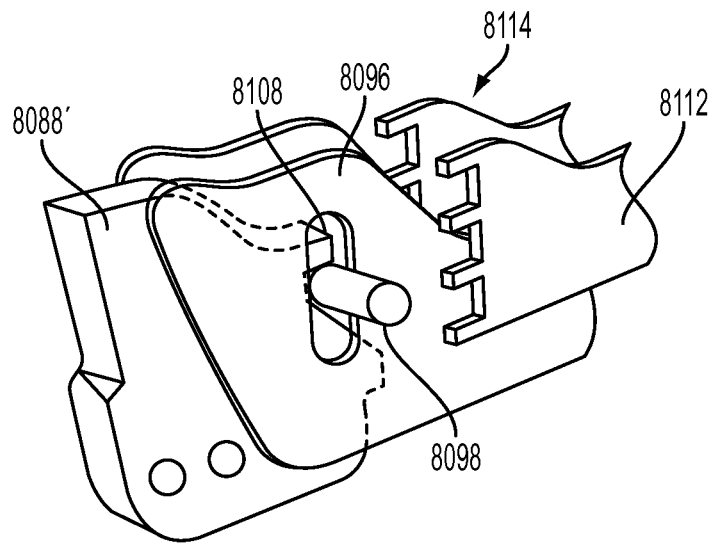
FIG. 23 is a perspective view of the second cutting element, I-beam, and push rod of FIG. 22.
Figure 24:
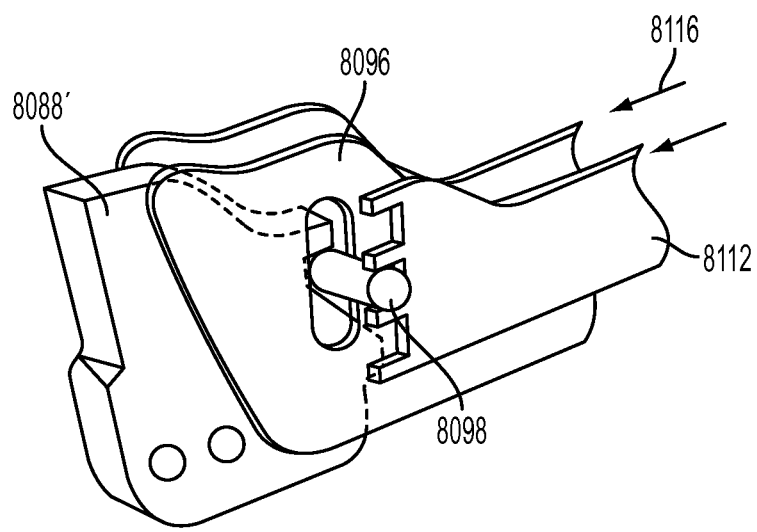
FIG. 24 is a perspective view of the second cutting element and the I-beam removably coupled to the push rod of FIG. 23.

FIG. 22, FIG. 23, and FIG. 24 illustrate one embodiment of a push rod 8112 configured to removably couple to the guide pin 8098 to facilitate engagement of the pin 8098 with the cutting element 8088'. Although the push rod 8112 is shown with the I-beam 8096 and the cutting element 8088' of FIG. 19, the push rod 8112 can be similar used with other I-beams and other cutting elements. The push rod 8112 can have a variety of sizes, shapes, and configurations. As in this illustrated embodiment, the push rod 8112 can include an elongate bar having a forked distal end 8114. The fork's tines can define spaces therebetween, each of which can be configured to removably seat the pin 8098 therein. The forked distal end 8114 in this illustrated embodiment includes four tines defining three spaces therebetween, but a push rod can include another plural number of tines to define at least one space.

In use, after the cartridge including the cutting element 8088' has been seated in the end effector so as to mate the pin 8098 with the cutting element's mating feature, as shown in FIG. 22 and FIG. 23, the push rod 8112 can be advanced in a distal direction 8116 until the forked distal end 8114 engages the pin 8098 so as to seat the pin 8098 in one of the spaces. FIG. 24 shows the pin 8098 seated in the depression 8092' and seated in a middle one of the push rod's spaces. Continued movement of the push rod 8112 in the distal direction 8116 can cause the I-beam 8096 and the sled including the cutting element 8088' to advance distally, thereby firing fasteners from the cartridge.

In some embodiments, a surface of a cartridge can be configured to define a gap of space between a bottom jaw and an anvil coupled thereto. As discussed herein, the cartridge can be configured to be removably coupled to an end effector that includes the bottom jaw and the anvil. The cartridge can thus be configured to define the gap of space.

Figure 25:
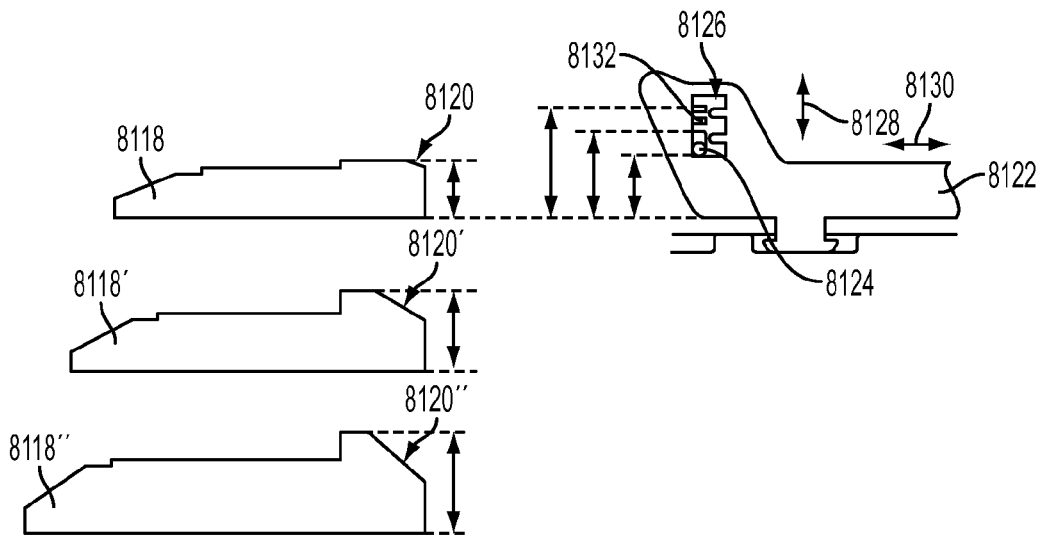
FIG. 25 is a side view of first, second, and third embodiments of a cartridge configured to removably couple to an I-beam.

FIG. 25 illustrates one embodiment of a cartridge 8118 configured to define a gap of space (not shown) between jaws of an end effector (not shown). In general, the cartridge 8118 can cooperate with an I-beam 8122 removably engageable with the cartridge 8118 to define the gap of space. The cartridge 8118 can include a proximal sloped surface 8120 that slopes upward in a distal direction. The sloped surface 8120 can be configured to engage a guide pin 8124 of the I-beam 8122 to facilitate positioning of the guide pin 8124 relative to the cartridge 8118 and, hence, to an anvil 8119, shown in FIG. 28. The guide pin 8124 of the I-beam 8122 can be configured to be movable relative to a remainder of the I-beam 8122.

Figure 26:
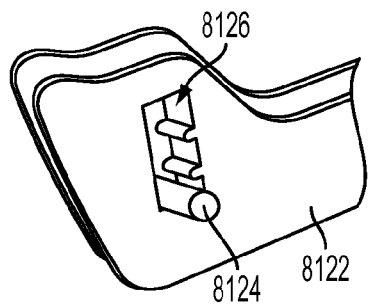
FIG. 26 is a perspective view of a distal portion of the I-beam of FIG. 25.
Figure 27:
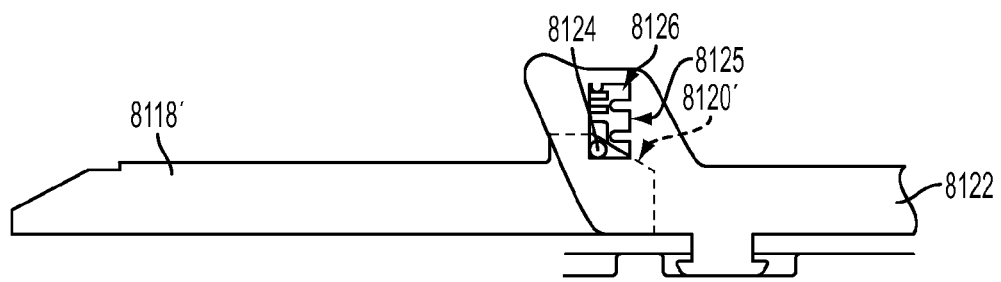
FIG. 27 is a perspective view of the second cartridge of FIG. 25 removably coupled to the I-beam, the second cartridge being partially seated in an end effector.

As in the illustrated embodiment, the I-beam 8122 can include an I-beam pin slot 8126 in which the pin 8124 can be configured to move. The I-beam 8122 can include a bias element 8132 configured to bias the pin 8124 toward a bottom surface of the slot 8126, as shown in FIG. 25 and in FIG. 26. The bias element 8132 includes a coil spring in this illustrated embodiment, but the bias element 8132 can have other configurations. The pin slot 8126 can extend in an upward/downward or vertical direction 8128 that can be substantially perpendicular to a proximal/distal direction 8130 in which the I-beam 8122 can be configured to translate through the cartridge 8118. The pin slot 8126 can include a plurality of notches formed therein on a proximal side thereof, as also shown in FIG. 27. The pin slot 8126 includes three notches in this illustrated embodiment, but a pin slot can include another number of notches. Each of the notches can be configured to seat the pin 8124 therein, the one of the notches depending on the sloped surface 8120 of the cartridge 8118. The pin 8124 can thus be configured to move in the slot 8126 in the upward/downward direction 8128 and in the proximal/distal direction 8130.

The pin 8098 can be configured to engage the sloped surface 8020 when the cartridge 8118 is removably coupled to the end effector that is attached to an elongate shaft (not shown) along which the I-beam 8122 extends. The pin 8124 can be configured to engage and slide upward and distally along the sloped surface 8020 until the pin 8124 reaches a top end of the sloped surface 8020, e.g., until the sloped surface 8020 ends. The force of the sloped surface 8020 on the pin 8124 can exceed a force provided by the bias element 8132, thereby allowing the pin 8124 to slide along the sloped surface 8020 and move upward within the slot 8126. When the pin 8124 reaches the top end of the sloped surface 8020, e.g., when the cartridge 8118 has been fully seated in the end effector, the pin 8124 can automatically move proximally so as to be seated in one of the notches. With the pin 8124 seated in the one of the notches, the I-beam 8122 can be advanced distally so as to fire fasteners (not shown) from the cartridge 8118 with the tissue gap defined by the pin's vertical location within the slot 8126.

Figure 28:
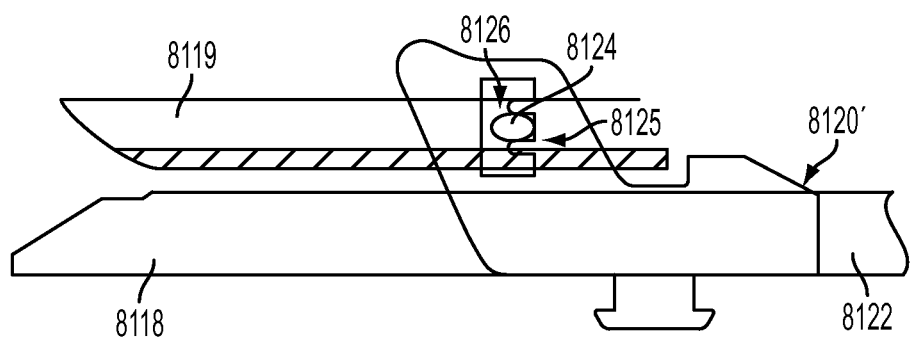
FIG. 28 is a side cross-sectional view of the second cartridge of FIG. 27 removably coupled to the I-beam and fully seated in the end effector.

FIG. 25 illustrates another embodiment of a cartridge 8118' that can be configured and used similar to the cartridge 8118. FIG. 25 also illustrates another embodiment of a cartridge 8118" that can be configured and used similar to the cartridge 8118. In this illustrated embodiment, the cartridge 8118 has a first size, e.g., a first longitudinal length and a first height, the cartridge 8118' has a second size, e.g., a second longitudinal length greater than the first longitudinal length and a second height greater than the first height, and the cartridge 8118" has a third size, e.g., a third longitudinal length greater than the second longitudinal length and a third height greater than the second height. The sloped surfaces 8120, 8120', 8120" of the cartridges 8118, 8118', 8118", respectively, can all start at a same location in a downward direction, thereby facilitating engagement of the pin 8124 with the sloped surface of the cartridge loaded into the surgical device's end effector. The cartridge 8118' has a longer and steeper ramped surface 8120' than the cartridge 8118 such that the pin 8124 can move into one of the notches at a higher location than with the cartridge 8118. The pin 8124 seated in a middle one of the notches 8125 in response to the cartridge 8118', as shown in FIG. 28, can thus be up higher than the pin 8124 when using the cartridge 8118. The tissue gap can thus be greater when using the cartridge 8118' versus the cartridge 8118. The cartridge 8118" has a longer and steeper sloped surface 8120" than the cartridge 8118 and the other cartridge 8118' such that the pin 8124 can move into one of the notches at a higher location than with the cartridge 8118 and than with the cartridge 8118'. The pin 8124 seated in the notch in response to the cartridge 8118" can thus be up higher than the pin 8124 when using either of the cartridge 8118, 8118'. The tissue gap can thus be greater when using the cartridge 8118" versus the cartridge 8118 and versus the cartridge 8118'.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical fastening device, comprising:
   an elongate shaft;
   an end effector coupled to a distal end of the elongate shaft, the end effector including a cartridge jaw and an anvil pivotally coupled to one another and movable between an open position and a closed position in which tissue can be engaged therebetween, wherein a distance between a proximal end of each of the cartridge jaw and the anvil is adjustable; and
   a cartridge removably seated within a channel in the cartridge jaw of the end effector, the cartridge including an anvil coupling member slidably disposed therein and configured to couple to a drive shaft extending through the elongate shaft for advancing the anvil coupling member distally through the end effector, wherein the anvil coupling member is configured to pivot away from the anvil when the anvil coupling member is positioned at a distal-most end of the anvil.

2. The device of claim 1, wherein the anvil coupling member engages and distally advances through a slot formed in the anvil, and wherein a distal end of the anvil includes an opening formed therein for releasing the anvil coupling member to allow the anvil to be moved to an open position away from the cartridge jaw.

3. The device of claim 1, wherein a proximal end of the anvil coupling member includes a feature formed therein for receiving a corresponding feature formed in a distal end of the drive shaft.

4. The device of claim 1, wherein the anvil coupling member includes a knife formed on a distal-facing surface thereof for cutting tissue engaged between the cartridge jaw and the anvil.

5. The device of claim 1, wherein the drive shaft includes a mating element formed on a distal end thereof that engages and slides within a slot formed in the cartridge jaw.

6. The device of claim 1, wherein the anvil coupling member includes a pin extending therethrough and protruding from lateral sides thereof, the pin being configured to engage and slide within a slot formed in the anvil of the stapling device.

7. The device of claim 1, wherein the cartridge includes a shim configured to define the distance between the proximal end of each of the cartridge jaw and the anvil.

* * * * *